(12) United States Patent
Johnson et al.

(10) Patent No.: US 10,324,020 B2
(45) Date of Patent: Jun. 18, 2019

(54) FLUIDIC OPTICAL CARTRIDGE

(71) Applicant: Palo Alto Research Center Incorporated, Palo Alto, CA (US)

(72) Inventors: David M. Johnson, San Francisco, CA (US); Noble M. Johnson, Menlo Park, CA (US); Michael I. Recht, Mountain View, CA (US); Joerg Martini, San Francisco, CA (US); Tim Curley, San Carlos, CA (US); Peter Kiesel, Palo Alto, CA (US); Martin Sheridan, Redwood City, CA (US)

(73) Assignee: Palo Alto Research Center Incorporated, Palo Alto, CA (US)

( * ) Notice: Subject to any disclaimer, the term of this patent is extended or adjusted under 35 U.S.C. 154(b) by 210 days.

(21) Appl. No.: 14/139,317

(22) Filed: Dec. 23, 2013

(65) Prior Publication Data
US 2015/0177118 A1  Jun. 25, 2015

(51) Int. Cl.
*G01N 15/14* (2006.01)
*B01L 3/00* (2006.01)

(52) U.S. Cl.
CPC ..... *G01N 15/1459* (2013.01); *G01N 15/1436* (2013.01); *G01N 2015/145* (2013.01)

(58) Field of Classification Search
None
See application file for complete search history.

(56) References Cited

U.S. PATENT DOCUMENTS

| 4,251,733 | A |   | 2/1981  | Hirleman, Jr. |
|-----------|---|---|---------|---------------|
| 5,272,354 | A | * | 12/1993 | Kosaka ........................ 250/574 |
| 5,422,712 | A |   | 6/1995  | Ogino |
| 5,444,527 | A |   | 8/1995  | Kosaka |
| 6,228,652 | B1| * | 5/2001  | Rodriguez ............. G01N 15/14  356/335 |
| 7,016,022 | B2| * | 3/2006  | Fritz .................... G01B 11/272  356/338 |
| 7,262,838 | B2|   | 8/2007  | Fritz |
| 7,540,205 | B2|   | 6/2009  | Nelson et al. |
| 7,688,427 | B2|   | 3/2010  | Cox et al. |

(Continued)

FOREIGN PATENT DOCUMENTS

WO  WO2013/085797  6/2013

OTHER PUBLICATIONS

File History for U.S. Appl. No. 14/139,246 as retrieved from the U.S. Patent and Trademark Office.

*Primary Examiner* — Neil N Turk
(74) *Attorney, Agent, or Firm* — Hollingsworth Davis, LLC

(57) ABSTRACT

Embodiments are directed to an apparatus that includes a fluidic structure and optical components. The fluidic structure includes a transparent channel through which objects in an analyte fluid can travel along respective paths during operation of the apparatus. The optical components are configured to provide measurement light to the objects traveling through the transparent channel. The fluidic structure is configured to reversibly engage with a host structure. The host structure includes a source of the measurement light and electronics to receive and process output light emanating from the objects traveling in the channel. The fluidic structure makes an air-tight seal when engaged with the host structure.

17 Claims, 19 Drawing Sheets

(56) References Cited

U.S. PATENT DOCUMENTS

| | | |
|---|---|---|
| 8,122,779 B2 | 2/2012 | Nelson et al. |
| 8,263,955 B2 | 9/2012 | Kiesel et al. |
| 8,373,860 B2 | 2/2013 | Kiesel et al. |
| 8,435,738 B2 | 5/2013 | Holmes et al. |
| 8,475,739 B2 | 7/2013 | Holmes et al. |
| 8,512,650 B2 | 8/2013 | Jungheim et al. |
| 8,518,345 B2 | 8/2013 | Butz et al. |
| 8,524,170 B2 | 9/2013 | Petrek |
| 2003/0036206 A1* | 2/2003 | Chien et al. .................. 436/180 |
| 2003/0054558 A1* | 3/2003 | Kurabayashi ...... G01N 15/1404 436/63 |
| 2004/0145725 A1* | 7/2004 | Fritz ............................... 356/39 |
| 2006/0034728 A1* | 2/2006 | Kloepfer ............ A61B 5/14532 422/68.1 |
| 2008/0181827 A1 | 7/2008 | Bassler et al. |
| 2008/0183418 A1 | 7/2008 | Bassler et al. |
| 2010/0167412 A1 | 7/2010 | Xiao et al. |
| 2010/0288941 A1 | 11/2010 | Ayliffe et al. |
| 2011/0076205 A1 | 3/2011 | Kelly et al. |
| 2011/0171754 A1* | 7/2011 | Redmond et al. ............ 436/518 |
| 2011/0222062 A1 | 9/2011 | Martini et al. |
| 2011/0291025 A1 | 12/2011 | Fortin et al. |
| 2012/0088230 A1* | 4/2012 | Givens et al. .................... 435/5 |
| 2012/0196314 A1 | 8/2012 | Nawaz et al. |
| 2013/0037726 A1 | 2/2013 | Kiesel et al. |
| 2013/0037728 A1 | 2/2013 | Kiesel et al. |
| 2013/0078625 A1 | 3/2013 | Holmes et al. |
| 2014/0170697 A1* | 6/2014 | Sharpe ............... G01N 15/1436 435/30 |

\* cited by examiner

FLUIDIC OPTICAL CARTRIDGE

TECHNICAL FIELD

Embodiments are directed to a fluidic optical cartridge configured to reversibly engage with a host structure useful as a component of a flow cytometer.

BACKGROUND

The present disclosure relates generally to articles and methods that involve the transmission and/or reflection of light emanating from objects. Various techniques have been proposed for analyzing light emanating from objects. One such technique describes a fluidic structure with a channel along which is a series of sensing components that can obtain information about objects traveling within the channel, such as droplets or other objects carried by fluid. A sensing component includes a set of detectors that can detect a range of photon energies that emanate from the objects. A processor can receive information about the objects from the sensing components and use the received information to obtain information about the objects. Analyzers with time variation based on coded spatial modulation have also been disclosed.

Flow cytometers have been developed that can utilize light emanating from objects, for example, biological particles, to determine particle size and to identify component particles in fluids such as, for example blood. Typically, the fluid is obtained from a living specimen and then is analyzed in a laboratory by a flow cytometer. Many such flow cytometers are known and are available but most of these flow cytometers are too large to be useful for point-of-use applications.

SUMMARY

Embodiments are directed to an apparatus that includes a fluidic structure and at least one optical component. The fluidic structure includes a channel through which objects can travel along respective paths during operation of the apparatus. The channel has at least one transparent wall. The optical component is configured to provide measurement light to the objects traveling through the channel. The fluidic structure is configured to reversibly engage with a host structure. The host structure includes a source of the measurement light and electronics to process output light emanating from the objects traveling in the channel.

Other embodiments include a method that includes engaging an apparatus with a pipettor tip. The apparatus includes a fluidic structure that includes a channel through which objects can travel along respective paths during operation of the apparatus, the channel having at least one transparent wall, and at least one optical component configured to provide measurement light to the objects traveling through the transparent channel. The fluidic structure is configured to reversibly engage with a host structure, the host structure including a source of the measurement light and electronics to process output light emanating from the objects traveling through the transparent channel. The method further includes drawing fluid into the transparent channel of the apparatus, directing measurement light onto objects traveling in the transparent channel, receiving output light emanating from the apparatus.

The above summary is not intended to describe each disclosed embodiment or every implementation of the present disclosure. The figures and the detailed description below more particularly exemplify illustrative embodiments.

BRIEF DESCRIPTION OF THE DRAWINGS

Throughout the specification reference is made to the appended drawings, where like reference numerals designate like elements, and wherein.

The figures are not necessarily to scale. Like numbers used in the figures refer to like components. However, it will be understood that the use of a number to refer to a component in a given figure is not intended to limit the component in another figure labeled with the same number.

DETAILED DESCRIPTION

Figure 1:
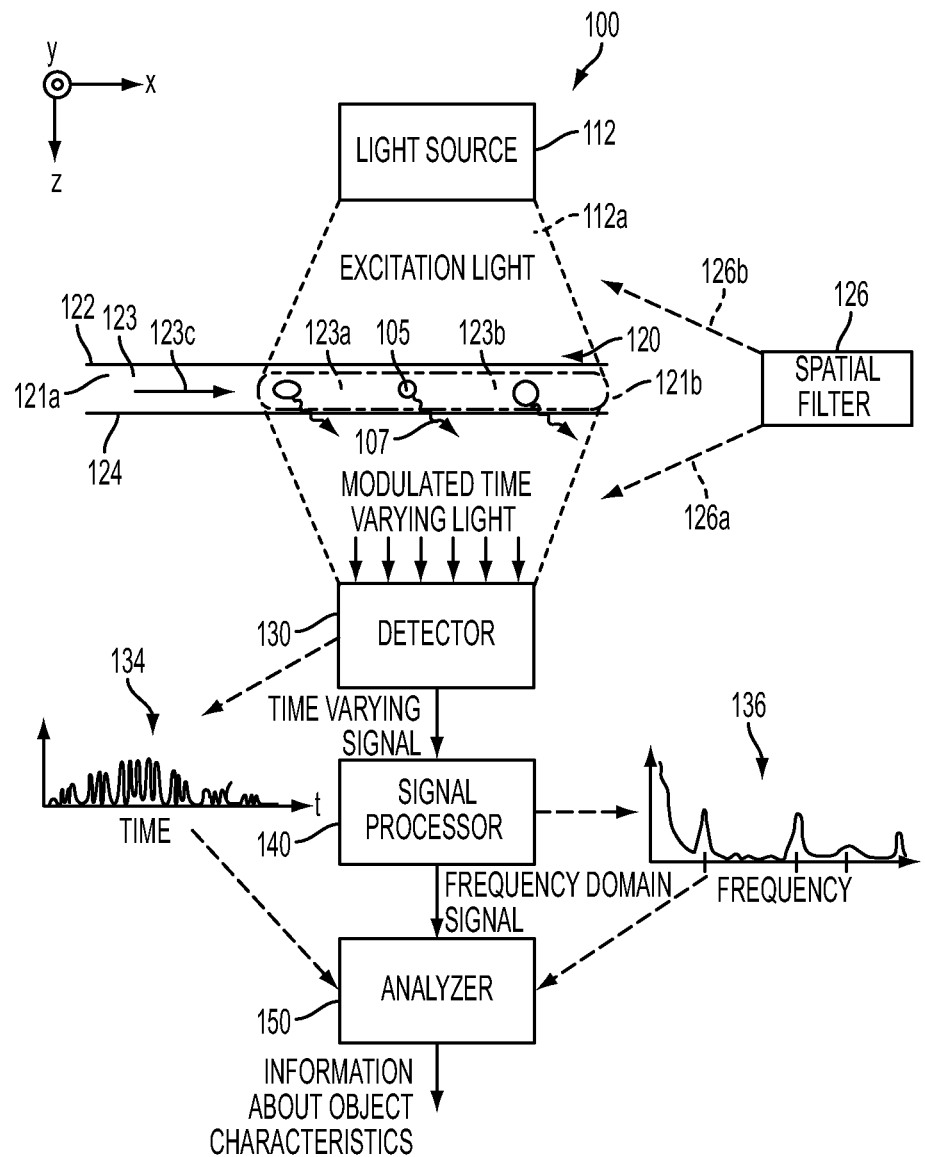
FIG. 1 is an example embodiment of an assembly with a spatial filter, detector, and analyzer configured to determine object characteristics based on spatially modulated light.

In the following description, reference is made to the accompanying set of drawings that form a part of the description hereof and in which are shown by way of illustration several specific embodiments. It is to be understood that other embodiments are contemplated and may be made without departing from the scope of the present disclosure. The following detailed description, therefore, is not to be taken in a limiting sense.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein. The use of numerical ranges by endpoints includes all real numbers within that range (e.g. 1 to 5 includes 1, 1.5, 2, 2.75, 3, 3.80, 4, and 5) and any range within that range.

The strategic landscape for biological and biomedical testing and analysis is undergoing a transformation. Today, the majority of tests are performed at major, centralized clinical laboratories. This is in part because compact, robust, and inexpensive instruments for point of care (POC) testing are not available. Principal drivers for POC testing are reducing costs, obtaining timely test results, lowering mortality rates, and reducing morbidity. Commercial flow cytometers are sophisticated analytical instruments extensively used in research and clinical laboratories. They do not, however, meet the challenging practical requirements of POC testing.

In conventional flow cytometry, the size of the excitation area is restricted approximately to the size of the particle to be detected. In contrast, the apparatus and methods disclosed herein may use a much larger excitation region to increase the total flux of detected light that emanates from a particle of interest. In combination with the large excitation area, spatial filtering can be employed to enable a high spatial resolution in the micron range. This may allow for independently detecting and characterizing particles with a separation (in the flow direction) that can approach the dimension of individual particles. Also, the disclosed apparatus and methods can be intrinsically tolerant to background light originating, for example, from fluorescent components in solution, fluorescent components of the detection apparatus, or surface contaminants.

The disclosed apparatus is a fluidic optical cartridge that can fit into a portable or hand-held host structure. In some embodiments, the host structure and the cartridge constitute a hand-held flow cytometer useful for POC testing. The cartridge can incorporate optics and fluid handling features of the cytometer and can be disposable. The cytometer can be used to analyze objects in a fluid, for example a biological fluid, at a point of care. The cytometer has a host structure that includes a compartment into which the disclosed apparatus can be reversibly engaged, where the term "reversibly engaged" indicates that the apparatus can be inserted and engaged in the compartment and later disengaged and extracted from the compartment. The host structure can include at least one light source, at least one waveguide to deliver measurement light to optics integrated into the cartridge, at least one detector to detect light emanating from the objects in the fluid to be analyzed and electronics to process signals from the detector and, optionally, can include either a display or can send the analysis to another external electronic device such as a computer, hand-held electronic device, or other electronic device by wire or wireless communication means. Details of a portable flow cytometer that includes the disclosed apparatus (fluidic optical cartridge) and a host structure can be found, for example, in U.S. Pat. No. 9,261,452, filed on the same day herewith. This co-filed application is herein incorporated by reference in its entirety.

The embodiments described herein can be useful for analysis to determine the dimensional characteristics of an object in a flow direction. The dimensional characteristics determination can be based on spatially modulated light emanating from the object. In particular, the techniques can make use of a spatial mask that can be deployed in a variety of applications, including analysis of system properties and/or detection of various characteristics of analyte in a sample. In some implementations, a non-imaging photodetector can be used to generate a time varying electrical output signal based on the spatially modulated light allowing for better compatibility with high-throughput cytometry. Some characteristics of the objects can include their type, the speed that they travel through the cytometer, their color, and their size. The combined measurements of many objects can allow for a characterization of a sample of objects, for example, by determination of object (particle) concentration in the sample.

It will be understood that the techniques, apparatuses, systems, and methods described herein are applicable to detect various objects such as analytes or particles present in a sample. The term "object" refers broadly to any object of interest to be detected. In some applications, objects of interest are particles or analytes that are relatively small, and may be microscopic in size. However, the techniques can be broadly applicable to objects of any size or shape. A given particle or analyte may be or include one or a collection of biological cell(s), virus(es), macromolecule(s) (including certain proteins or protein chains, DNA or RNA fragments), molecules, droplets (e.g. oil in water), gas bubbles, microparticles, nanoparticles, beads or other small particles that can bind and carry specific chemicals or other analytes.

In some embodiments, the disclosed apparatus can obtain information about objects by receiving signals from them; for example, signals in the form of light can emanate from an object, whether through emission (e.g. radiation, fluorescence, incandescence, chemiluminescence, bioluminescence, other forms of luminescence, etc.), scattering (e.g. reflection, deflection, diffraction, refraction, etc.), or transmission, and can be sensed by a photodetector. Cells or other particles may be treated, e.g., stained or tagged with a suitable (fluorescent) probe or other agent, in such a way that they emit light or absorb light in a predictable fashion when illuminated with measurement light. In this regard, the light emitted by a given excited particle may be fluorescent in nature, or it may constitute a form of scattered light such as in the case of Raman scattering. For simplicity, the light that emanates from (by e.g., scattering, emission, or transmission) by an object is referred to herein as "emanating light" or "light emanating." It will be understood that the techniques, assemblies, apparatuses, systems, and methods described herein are applicable to detecting all forms of light emanating from an object or constituent parts thereof. Techniques that can use filter arrangements to transmit and/or reflect light emanating from objects with time variation, such as when the objects are moving relative to the filter arrangements are disclosed, for example, in Applicants' U.S. Pat. Appl. Publ. No. 2011/0222062 A1 (Martini et al.), now allowed, which is herein incorporated by reference in its entirety.

FIG. 1 is an example of an assembly 100 configured to determine object characteristics based on spatially modulated light. Assembly 100 includes light source 112, spatial filter 126, a flow path, e.g., fluidic structure 120, detector 130, signal processor 140, and analyzer 150. Fluidic structure 120 is adapted to receive a sample of interest to be analyzed. The sample may enter the fluidic structure 120 at inlet 121*a* (that can be mated to, for example, an pipettor tip) and exit the fluidic structure 120 at outlet 121*b*, flowing generally along the x-direction through channel 123 formed between confining members 122 and 124 also referred to as "walls" (that can, in some embodiments, be opposite walls of a capillary tube). Channel 123 can have at least one transparent wall. Members 122, 124 may be or may comprise plates or sheets of glass, plastic, or other suitable transparent materials. Members 122 and 124 may or may not be planar in shape. For example, they may be portions of a unitary tube or pipe having a cross section that is circular, rectangular, or another shape. Other non-planar shapes are also contemplated. In some cases, confinement of the sample may not be necessary, whereupon one or both of members 122 and 124 may be omitted. At least a portion of confining member 122 is transmissive to measurement light emitted by the light source 112 at least in an excitation region 123*a*. In that regard, light source 112 may emit measurement light 112 towards the fluidic structure 120.

In some cases, for example, light source 112 may include a conventional light-emitting diode (LED) source or a resonant cavity LED (RC-LED) source. If desired, the light source may incorporate one or more optical filters to narrow or otherwise tailor the spectrum of the resultant output light. Such optical filters can, for example, be bandpass filters. Whichever type of light source is selected, the spectral makeup or composition of the measurement light emitted by source 112 can be tailored to excite, to scatter, or otherwise to cause emanation of light from at least some of the objects that may be present in the sample, as discussed further below. Light source 112 may include a light-emitting diode, a superluminescent diode, a diode-pumped solid state laser, a frequency-doubled laser, a frequency-tripled laser, or even a frequency-quadrupled laser.

The sample is depicted as containing exemplary objects 105 of varying sizes and shapes. Objects 105 emanate light 107 in all directions (only some directions are illustrated). Objects 105 may have a variety of characteristics, some of which can be determined by analyzer 150 based on emanating light 107.

Detector 130 can receive time-varying light from objects 105 travelling in the channel as modulated by spatial filter 126 and can generate an electrical signal in response to the time varying light. The time variation in the light detected by detector 130 may be the result of interaction between the measurement light and an input spatial filter to create spatially patterned measurement light that illuminates object 105. Alternatively, the time variation in the light detected by detector 130 may be the result of interaction between light emanating from objects 105 and an output spatial filter as the objects travel through the channel along respective paths. In some embodiments, the detector includes an optical filter arranged between the detector and the objects. An optical filter can be particularly useful when the emanating light is fluorescent light and the optical filter is configured to substantially block the wavelengths of the measurement light and to substantially pass the wavelengths of the light emanating from the objects.

Assembly 100 of FIG. 1 includes spatial filter 126 (sometimes referred to as a mask) which can be positioned in various locations. The mask may be part of the fluidic device or may be part of a host structure. Dashed arrows 126*a* and 126*b* indicate possible locations of spatial filter 126 to provide spatially modulated light and/or modulated measurement light. In some configurations, indicated by arrow 126*a*, the spatial filter 126 can be disposed between flow channel 123 and detector 130. In this position, spatial filter 126 is referred to as an output spatial mask. In other configurations, indicated by arrow 126*b*, the spatial filter 126 can be disposed between the light source 112 and the flow channel 123. In this position, spatial filter 126 is referred to as an input spatial filter. An input spatial filter may be adapted to transmit light emitted by the light source by varying amounts along excitation region 123*a* of flow channel 123. In this configuration, the input spatial filter creates patterned measurement light in excitation region 123*a* of flow channel 123. According to various implementations, an input spatial filter may comprise a physical mask including a sequence or pattern of first regions that are more light transmissive and second regions that are less light transmissive. The input spatial filter may alternatively or additionally comprise micro-optics or a patterned light source configured to create the excitation pattern. The excitation pattern can be imaged and/or directed onto excitation region 123*a* using optical components for the imaging (e.g., lenses) and/or direction, (e.g., fiber optics or waveguides).

In some embodiments, an output spatial filter may be utilized and disposed between objects 105 and detector 130 at detection region 123*b* of the flow channel. In some embodiments, excitation region 123*a* and detection region 123*b* overlap. In other embodiments, there may be partial overlap between the excitation and detection regions or the excitation and detection regions may be non-overlapping or multiple detection regions and/or excitation regions may be used with various overlapping and/or non-overlapping arrangements. In assembly 100 shown in FIG. 1, the output spatial filter may be adapted to interact with light 107 emanating from objects 105 in flow channel 123. In some embodiments, the output spatial filter may be a physical mask comprising a sequence or pattern of first regions that are more light transmissive and second regions that are less light transmissive. In some embodiments, color spatial filters may be used such that a first region of the color spatial filter is more transmissive to a first wavelength band and less transmissive to a second wavelength band and a second region of the color spatial filter is less transmissive to the first wavelength band and is more transmissive to the second wavelength band. Analyzers with time variation based on color-coded spatial modulation are disclosed, for example, in U.S. Pat. Appl. Publ. No. 2011/0222062 (Martini et al.).

According to some embodiments of assembly 100 that include the input spatial filter, as object 105 travels in flow direction 123*c* in excitation region 123*a* of flow channel 123, light emanating from light source 112 is alternately substantially transmitted to object 105 and substantially blocked or partially blocked from reaching object 105 as object 105 travels along flow direction 123*c*. The alternate transmission and non-transmission (or reduced transmission) of measurement light 112 along flow direction 123*c* produces time-varying light 107 emanating from object 105. Time-varying light 107 emanating from object 105 falls on detector 130 and, in response, detector 130 generates time-varying detector output signal 134.

According to some embodiments of assembly 100 that include the output spatial filter configuration, light 112 from light source 112 illuminates object 105, causing object 105 to emanate light 107. As object 105 travels in flow direction 123*c* in detection region 123*b* of flow channel 123, the output spatial filter alternatively entirely or substantially blocks light 107 emanating from object 105 from reaching detector 130 and substantially transmits light 107 emanating from object 105 to detector 130. The alternate substantial transmission and blocking (or partial blocking) of light 107 emanating from object 105 as object 105 flows through detection region 123b produces time varying light that falls on detector 130. In response, detector 130 generates time-varying detector output signal 134.

In some embodiments such as the embodiment of FIG. 1, assembly 100 may include signal processor 140 that converts time-varying detector output signal 134 to frequency domain output signal 136 so as to provide spectral power as a function of frequency. Signal processor 140 may be part of detector 130 in some embodiments or may comprise separate circuitry in other embodiments. For example, in some embodiments, signal processor 140 may be part of analyzer 150 circuitry along with the detector. For conversion, signal processor 140 may use known techniques such as discrete Fourier transform including, for example, a Fast Fourier Transform "FFT" algorithm. Thus, frequency domain output signal 136 represents the frequency component magnitude of time-varying detector output signal 134, where the frequency component magnitude is the amount of a given frequency component that is present in time-varying detector output signal 134 or function. The Fourier signal power is a relevant parameter or measure because it corresponds to the function or value one would obtain by calculating in a straightforward manner the Fourier transform (e.g. using a Fast Fourier Transform "FFT" algorithm) of time-varying output signal 134. However, other methods or techniques of representing the frequency component magnitude, or other measures of the frequency component magnitude, may also be used. Examples may include e.g., the square root of the Fourier signal power, or the signal strength (as measured in voltage or current) obtained from a filter that receives as input time-varying detector output signal 134.

In FIG. 1, time-varying detector output signal 134 and/or frequency domain detector output signal 136 can be passed to analyzer 150. Analyzer 150 is configured to receive time-varying detector output signal 134 and/or frequency domain detector output signal 136 and to determine characteristics of object 105 in one or more dimensions including at least a size based upon time-varying detector output signal 134 and/or frequency domain detector output signal 136. As will be discussed subsequently, the various embodiments discussed herein provide examples of techniques for determining the size of object 105 using various mask designs and processing techniques.

Figure 2:
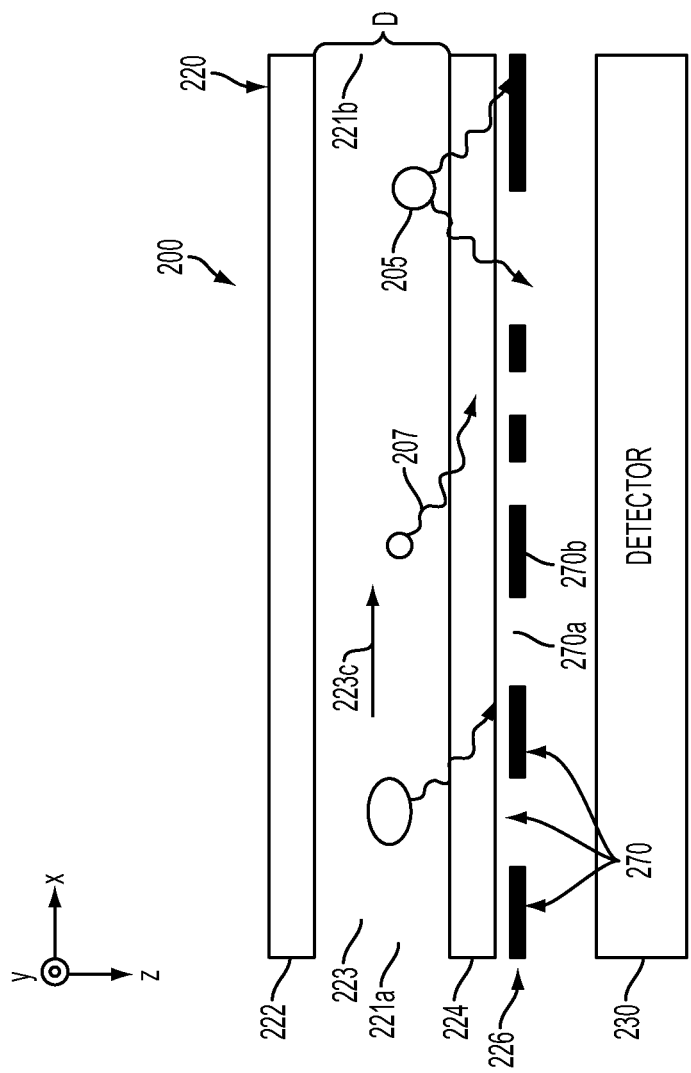
FIG. 2 is a schematic view of another example embodiment of an assembly with the spatial filter positioned between the object and the detector with the spatial filter spaced apart from the flow channel.

FIG. 2 is an enlarged schematic view of a portion of assembly 200 according to another example embodiment. The portion of assembly 200 illustrated in FIG. 2 includes a flow path, e.g., fluidic structure 220, detector 230, and spatial filter 226. Fluidic structure 220 is adapted to receive a sample of interest to be analyzed. The sample may enter the fluidic structure 220 at inlet 221a thereof, that can, in some embodiments, be a pipettor tip; and exit fluidic structure 220 at outlet 221b, flowing generally in flow direction 223c along the x-direction through flow channel 223 formed between confining members 222 and 224. As illustrated in FIG. 2, one or more objects 205 can be disposed at various locations within flow channel 223 and can have different sizes. As discussed previously, spatial filter 226 may comprise, for example, a spatial mask. As will be discussed in greater detail subsequently, spatial filter 226 may have a plurality of mask features 270. Mask features 270 can include light transmissive regions 270a and less transmissive regions 270b. The pattern or sequence of transmissive regions 270a and less transmissive regions 270b define a transmission function that changes based on the size and shape of the object. This transmission function may be substantially periodic, or it may instead be substantially non-periodic. The transmission function is sensed by detector 230, which is configured to output the time-varying output signal discussed in FIG. 1 in response.

In the embodiment of FIG. 2, spatial filter 226 may be substantially monochromatic or polychromatic as desired. In a monochromatic mask, transmissive regions 270a all have substantially the same transmission characteristic across a certain spectral region, and non-transmissive regions 270b also all have substantially the same transmission characteristic across this spectral region (but different from that of transmissive regions 270a). In a simple case, transmissive regions 270a may all be completely clear, as in the case of an aperture, and less transmissive regions 270b may be completely opaque, as in the case of a layer of black ink or other absorptive, reflective, or scattering material. Alternatively, transmissive regions 270a may all have a given color or filter characteristic, e.g., high transmission for light emanating from an excited object, but low transmission for measurement light. Alternatively, less transmissive regions 270b may have a low but non-zero light transmission, as in the case of a grey ink or coating, or a partial absorber or reflector.

Figure 3:
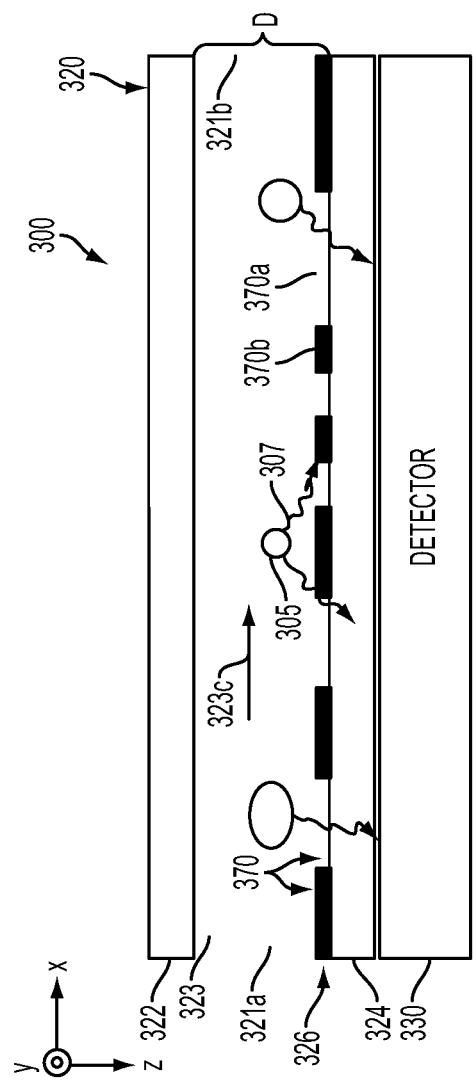
FIG. 3 is a schematic view of yet another example embodiment of an assembly with the spatial filter positioned between the object and the detector with the spatial filter positioned within the flow channel.
Figure 4:
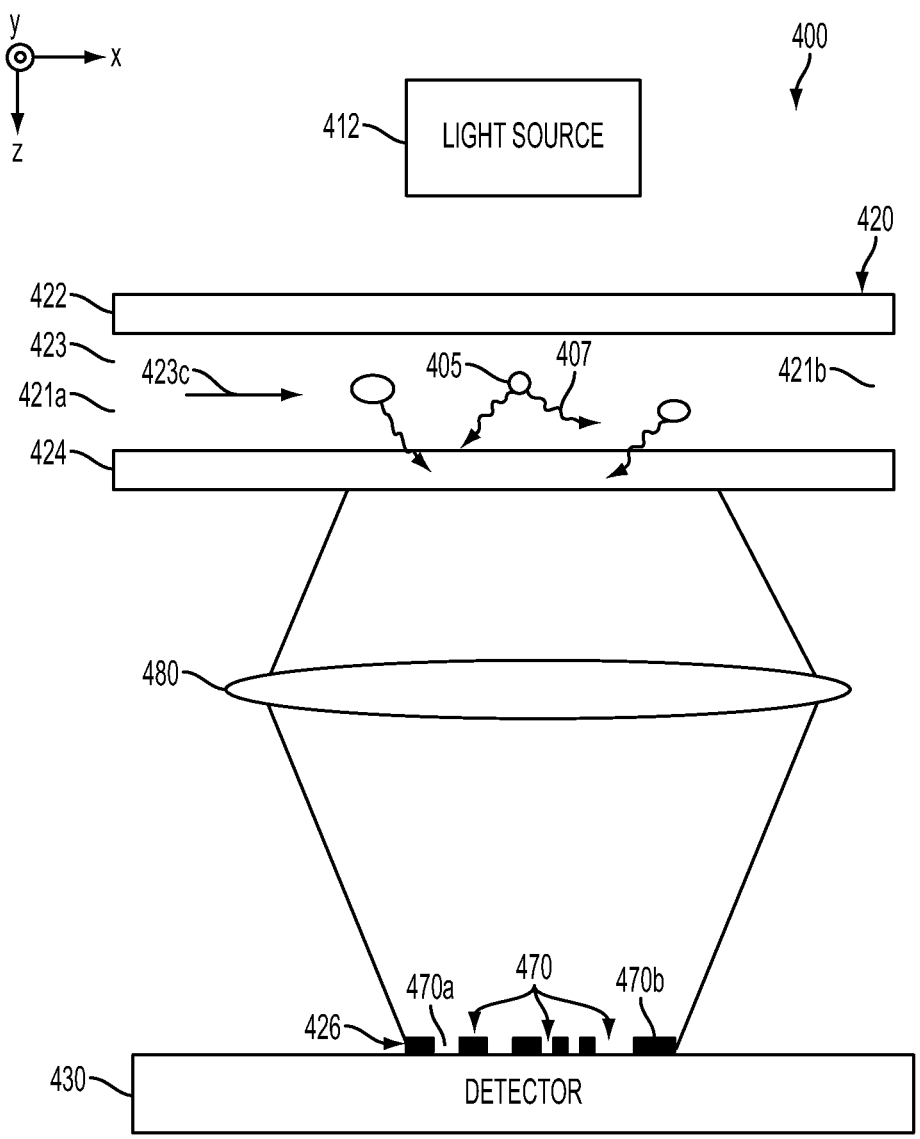
FIG. 4 is a schematic view of another example embodiment of an assembly with an optical imaging element positioned between the object and detector and the spatial filter positioned adjacent the detector.

In the embodiment of FIG. 2, spatial filter 226 is positioned between objects 205 and detector 230. Light 207 emanating from objects 205 interacts with spatial filter 226 to provide modulation of the sensed light that falls on detector 230. In the illustrated embodiment, spatial filter 226 can be positioned between objects 205 and detector 230 and spatial filter 226 and detector 230 and can be spaced apart from flow channel 223 (and confining member 224), e.g., by a distance greater than a depth D of flow channel 223. FIG. 3 is an enlarged schematic view of a portion of assembly 300 according to another example embodiment. The portion of assembly 300 illustrated includes a flow path, e.g., fluidic structure 320, detector 330, and spatial filter 326. Similar to the embodiments of FIGS. 1 and 2, structure 320 includes inlet 321a, outlet 321b, flow channel 323 having a flow direction 323c, and confining members 322 and 324. As illustrated in FIG. 2C, one or more objects 305 have different shapes and/or sizes in the x and z directions and are disposed within flow channel 323. Spatial filter 326 includes mask features 370 with light transmissive regions 370a and less transmissive regions 370b. In the embodiment of FIG. 3, spatial filter 326 is positioned between objects 305 and detector 330. However, spatial filter 326 is positioned proximate to or within flow channel 323. FIG. 4 is a schematic view of another embodiment of a portion of assembly 400 according to another example of remote sensing. The portion of assembly 400 illustrated includes light source 412, spatial filter 426, flow path, e.g., fluidic structure 420, and detector 430. Similar to the embodiments of FIGS. 1, 2, and 3, fluidic structure 420 includes inlet 421a, outlet 421b, flow channel 423 having flow direction 423c, and confining members 422 and 424. Spatial filter 426 includes mask features 470 with light transmissive regions 470a and less transmissive regions 470b. In FIG. 4, spatial filter 426 is positioned between objects 405 and detector 430 and is positioned remotely from flow channel 423 immediately adjacent detector 430. Optical imaging element 480 such as, for example, a lens, microlens array, or micromirror array, is positioned between objects 405 and filter 426 and is configured to image light from objects 405 onto at least one of spatial filter 426 and detector 430. The light emanating from objects 405 and imaged by element 480 interacts with spatial filter 426 to provide modulation of the sensed light received by detector 430.

Figure 5:
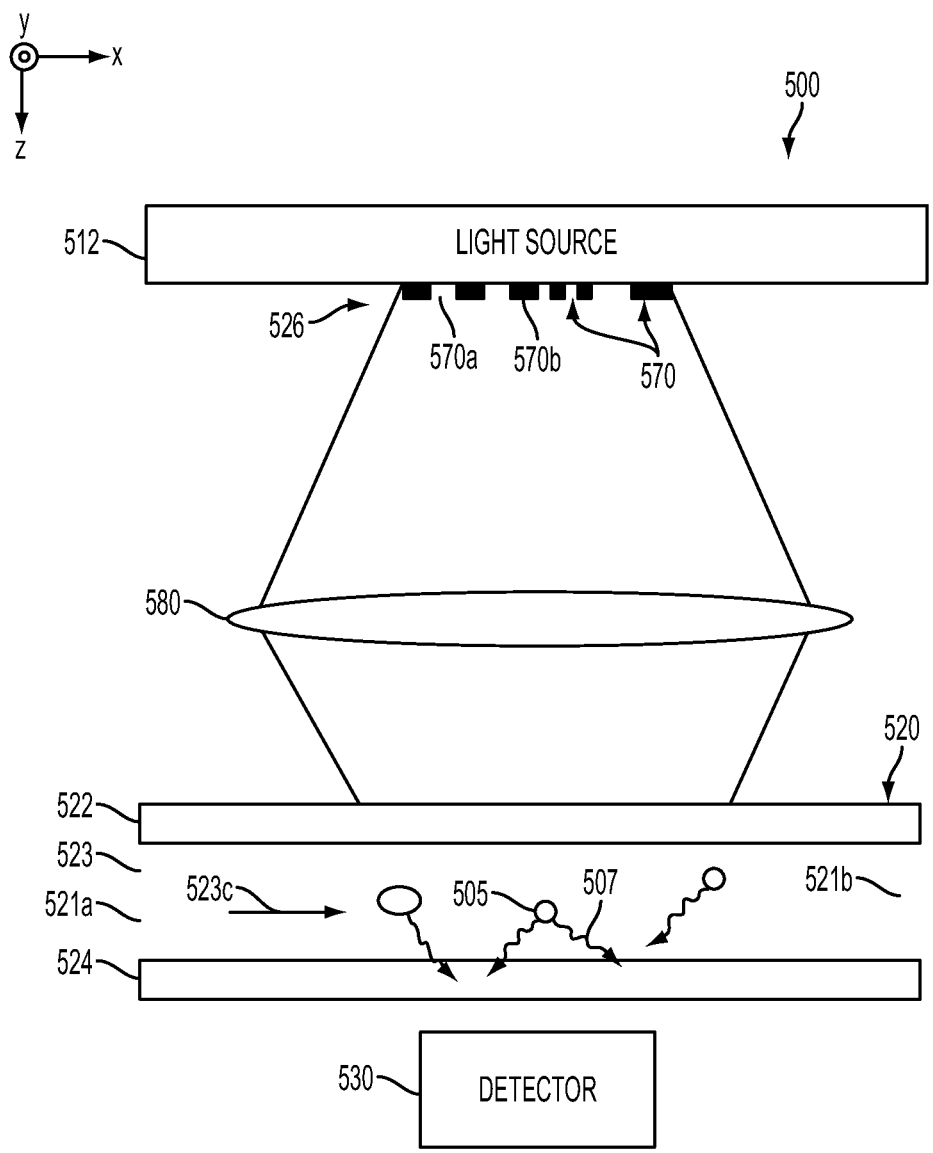
FIG. 5 is a schematic view of another example embodiment of an assembly with the optical imaging element positioned between the light source and the detector and the spatial filter positioned adjacent the light source.

FIG. 5 is a schematic view of yet another embodiment of a portion of assembly 500. The portion of assembly 500 illustrated includes light source 512, spatial filter 526, a flow path, e.g., fluidic structure 520, and detector 530. Similar to the previously discussed embodiments, fluidic structure 520 includes inlet 521a, outlet 521b, flow channel 523 having flow direction 523c, and confining members 522 and 524. Spatial filter 526 includes mask features 570 with light transmissive regions 570a and less transmissive regions 570b. In FIG. 5, spatial filter 526 is positioned between light source 512 and fluidic structure 520 containing objects 405. As shown, spatial filter 526 is positioned remotely from flow channel 523 immediately adjacent light source 512. Interaction between the output light from light source 512 and spatial filter 526 causes spatially modulated measurement light 512. Optical imaging element 580 is positioned between filter 526 and objects 505 and is configured to image spatially modulated measurement light 512 onto an excitation region of flow channel 523. Additionally, optical imaging element 580 may incorporate one or more filters to narrow or otherwise tailor the spectrum of the resultant spatially modulated measurement light. The spatially modulated measurement light causes light 507 emanating from objects 505 to be spatially modulated as well. The spatially modulated light emanating from objects 505 sensed by the detector 530. Due to the movement of objects 505 through flow channel 523, the emanating light 507 is modulated in time.

Figure 6:
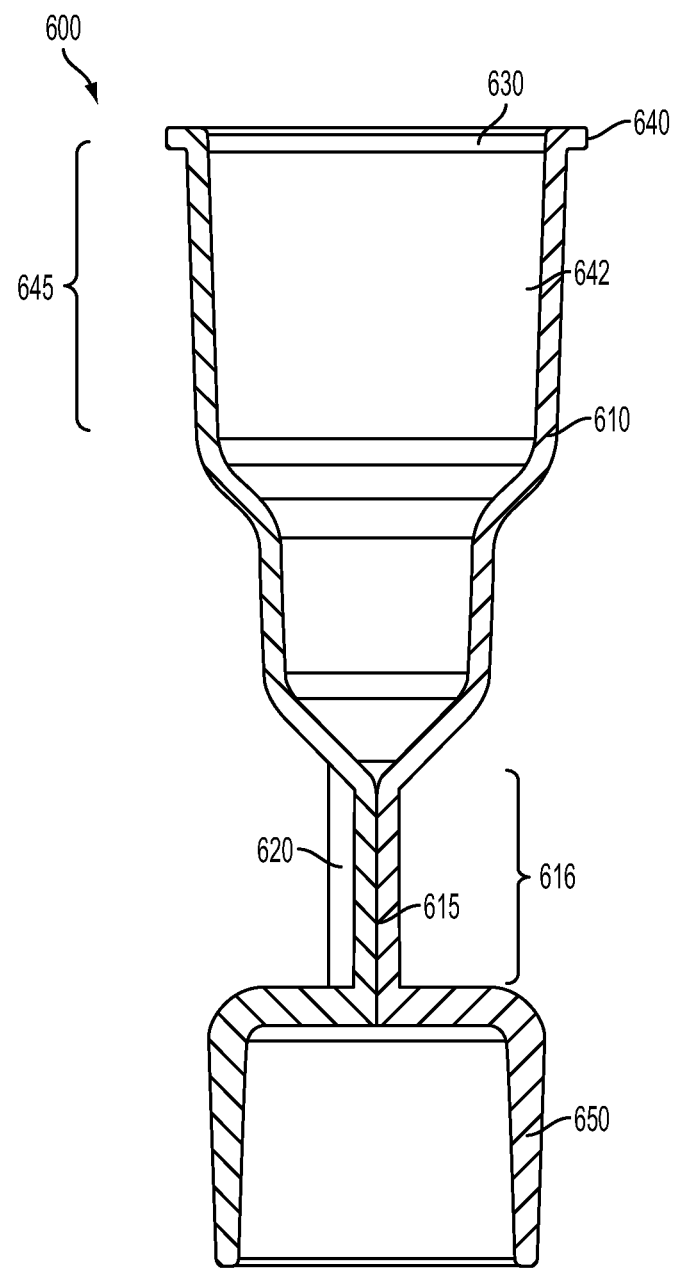
FIG. 6 is a side cut-away view of an apparatus according to an example embodiment.

FIG. 6 is a side cutaway view of an apparatus according to an example embodiment. Apparatus or cartridge 600 includes fluidic structure 610. Fluidic structure 610 includes transparent channel 615 through which objects in a fluid can travel along respective paths during operation of apparatus 600. Apparatus 600 also includes optical component 620 (partially behind transparent channel 615 in FIG. 6 but visible in FIG. 7. Optical component 620 can include a light-redirecting element. In the embodiment shown in FIG. 6, the light-redirecting element is a lens element that can redirect measurement light from an outside source (host structure) to the objects traveling through the transparent channel within transparent optical region 616.

Apparatus 600 can be made of transparent polymeric material such as, for example, poly(methyl methacrylate), polycarbonate, polypropylene, or polyethylene. In some embodiments at least one wall of transparent optical region 616 need be transparent and the remainder of apparatus 600 can be made of other materials.

Apparatus 600 can be reversibly engaged with a host structure. The host structure (not shown) can include a light source, a waveguide to deliver light to transparent channel 615, and an air piston configured to provide air (or vacuum) to apparatus 600 to control fluid movement into and out of apparatus 600. Accordingly, apparatus 600 includes flange 640 that is configured to reversibly engage with a host structure. In FIG. 6, feature 645 can be taper 642, a female tapered feature designed to fit into a male tapered part of the host structure. In some embodiments, a projecting male tapered part of the host structure, such as an air piston, can fit snugly into taper 642 and/or can include geometry to seal the projecting male tapered part of the host structure with the taper 642. The seal can be snug enough to allow air or vacuum to control fluid movement into and out of apparatus 600.

Apparatus 600 also includes mating end 650 (pictured in FIG. 6 as a tapered female socket, but not limited to that feature) that is configured to engage a pipettor tip. Typical pipettor tips have various mating features such as, for example, repositionable tip fitting mounting shafts, coupling elements, mounting segments, or tapers. Mating end 650 can be designed to fit any disposable pipettor tips and can have appropriate button shaft stopping features and, if present in the pipettor tip, interlocking features. Mating end 650 can be configured to fit repositionable pipettor tips made by Rainin Instrument, LLC (Oakland, Calif.), Eppendorf A G, Hamburg, GERMANY, Quigen GmbH, Hilden, GERMANY, Thermo-Fisher (Minneapolis, Minn.), Hoffman La Roche (Basel, Switzerland), Gilson (Middleton, Wis.), Hamilton Company (Reno, Nev.), and Viaflow Corporation, Hudson, N.H. It is also contemplated that the disclosed apparatus can be adapted to and utilized with multi-channel or single-channel pipettors (pipettes). Such multi-channel pipettors are available, for example, from many of the sources listed above and also from Sartorius, Bohemia, N.Y. under the tradename BIOHIT PROLINE, BIOHIT m-LINE, or BIOHIT e-line. The disclosed apparatus or a plurality of disclosed apparatuses can also be adapted to robotic liquid handling systems such as, for example, those available under the tradename EVO by the Tecan Systems, Inc., San Jose, Calif.

Figure 7:
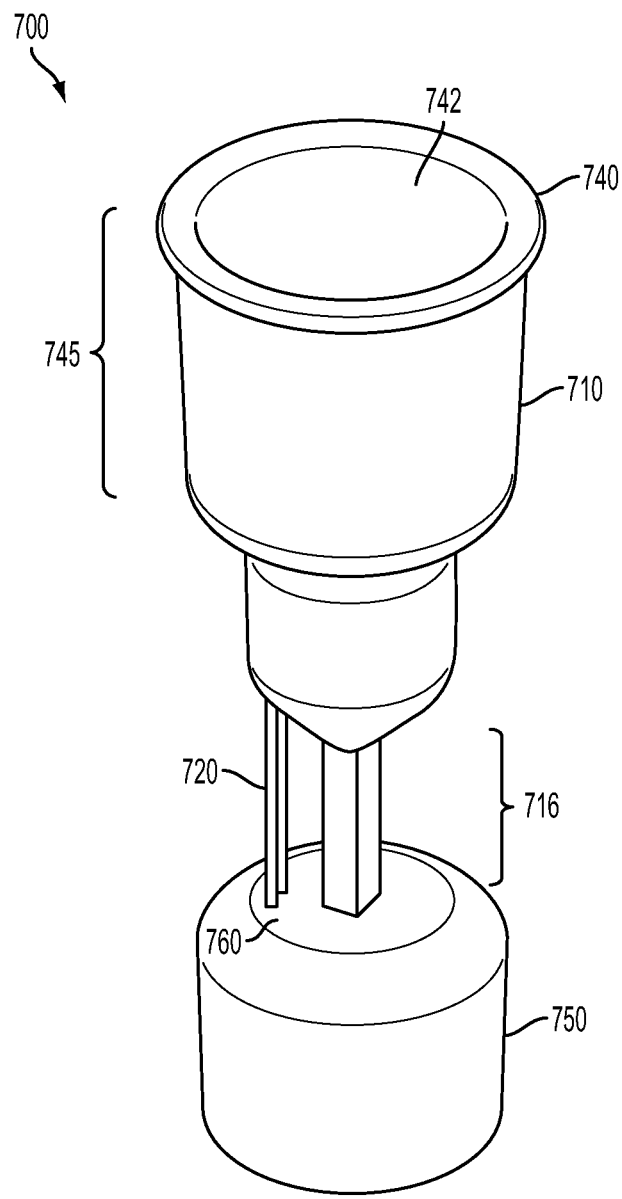
FIG. 7 is a perspective view of the apparatus shown in FIG. 6.

FIG. 7 is a perspective view of the apparatus illustrated in FIG. 6 showing some of the features more clearly. Apparatus or cartridge 700 includes fluidic structure 710. Fluidic structure 710 includes transparent optical region 716 concealing a channel (not visible in FIG. 7) through which objects in a fluid can travel along respective paths during operation of apparatus 700. Apparatus 700 also includes optical component 720. Optical component 720 can include a light-redirecting element. In the embodiment shown in FIG. 7, the light-redirecting element is a lens element that can redirect measurement light from an outside source (host structure) to the objects traveling through the transparent channel within transparent optical region 716. In some other embodiments, light-redirecting element of optical component 720 can include light shaping elements such as lens arrays or mirror arrays.

Apparatus 700 can be reversibly engaged with a host structure. The host structure (not shown) can include a light source, a waveguide to deliver light to the transparent channel in transparent optical region 716, and an air piston configured to provide air (or vacuum) to apparatus 700 to control fluid movement into and out of air displacement pipettors attached to apparatus 700. Apparatus 700 includes flange 740 that is configured to reversibly engage with a host structure. In FIG. 7, feature 745 can be taper 742, a female tapered feature designed to fit into a male taper in the host structure. In some embodiments, a projecting male tapered part of the host structure, such as an air piston, can fit snugly into taper 742 and can make a seal at taper 742 with apparatus 700.

Apparatus 700 also includes mating end 750 that is configured to engage a pipettor tip. Typical pipettor tips have various mating features such as, for example, repositionable tip fitting mounting shafts, coupling elements, mounting segments, or tapers. Mating end 750 can be designed to fit any disposable pipettor tips and can have appropriate button shaft stopping features and, if present in the pipettor tip, interlocking features that complement the pipettor tip. Both transparent optical region 716 of fluidic structure 710 and optical component 720 are fixed to a common base plate 760. The optical component and the transparent optical region are in a fixed spatial relationship with each other facilitating the use of the cartridge in the host structure since important optical alignments in the cartridge are molded into the piece. In some embodiments, the fluidic structure and the optical component can be molded as one piece. Any other permanent alignment may also serve the same purpose.

Figure 8A:
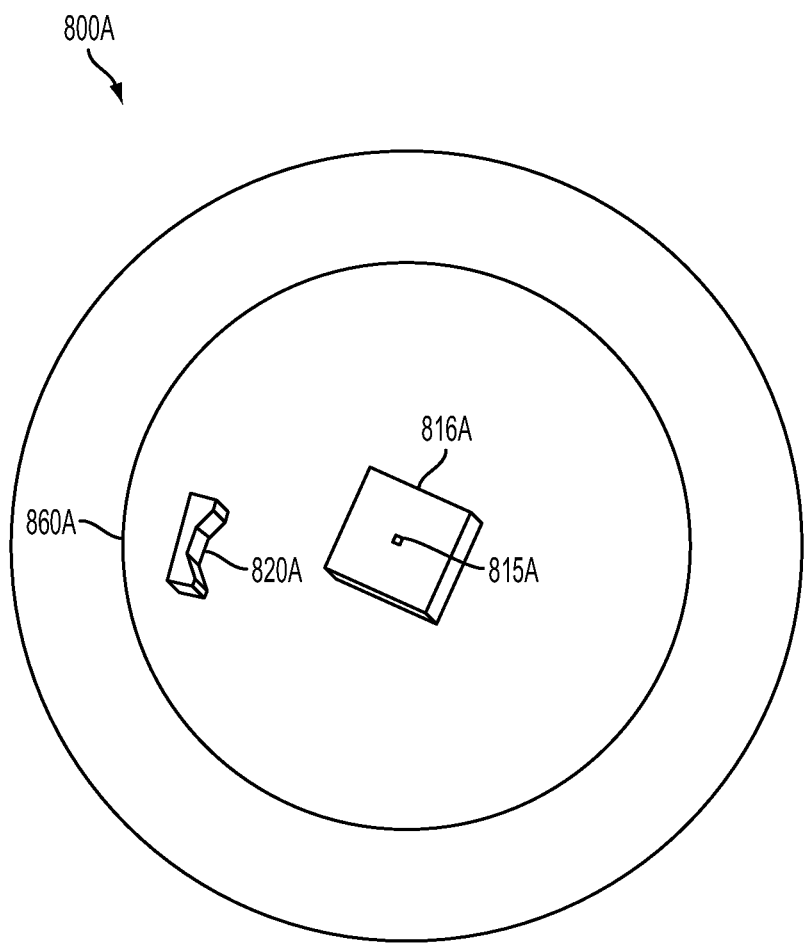
FIGS. 8A-8D are cut-away top down views of various example embodiment of the apparatus shown in FIG. 7.

FIG. 8A is a top down view of base plate 760 shown in FIG. 7. Base plate 860A is connected to transparent optical region 816A (cross-section shown in FIG. 8A that also shows transparent fluidic channel 815A) and optical component 820A. In the embodiment illustrated in FIG. 8A, optical component 820A is shown as a concave reflecting mirror (light-redirecting element), but, as mentioned above, any other optical component that modifies the measurement light and delivers the modified light through transparent optical region 816A into fluidic channel 815A. For example, optical component 820A can be any combination of, but not limited to, lenses, mirrors, prisms, gratings, phase retardation plates, or optical modulation devices. Optical component 820A is at a fixed position with respect to transparent optical region 816A (and transparent fluidic channel 815A). The critical optical alignment between optical component 820A and transparent fluidic channel 815A has designed into apparatus 800A by attaching them in a fixed position on base plate 860A. In the example embodiment illustrate in FIG. 8A, there is one optical component 820A and one transparent optical region 816A.

Figure 8B:
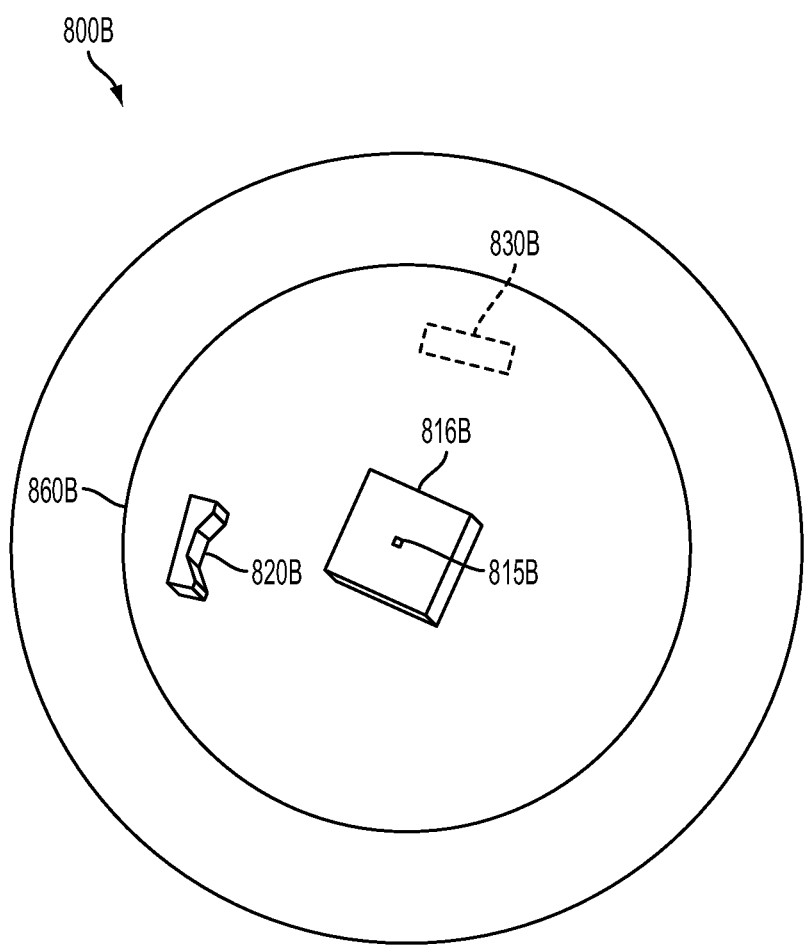

FIG. 8B shows another example embodiment of a disclosed apparatus. Base plate 860B is connected to transparent optical region 816B (cross-section shown in FIG. 8B that also shows transparent fluidic channel 815B) and optical component 820B. In the embodiment illustrated in FIG. 8B, optical component 820B is shown as a concave reflecting mirror (light-redirecting element), but, as mentioned above, any other optical component that modifies the measurement light and delivers the modified light through transparent optical region 816B into fluidic channel 815B. Apparatus 800B in FIG. 8B also includes filter assembly 830B that can take output light emanating from the objects travelling in the channel and modify it before it reaches detectors in the host structure. In some embodiments, the filter assembly can be a mask that is directly in contact with transparent optical region 816B. Filter assembly 830B can be located on base plate 860B and can include encoding components, decoding components, imaging components, spatial filters, masks, and a combination of these features. In some embodiments, the encoding components and/or decoding components can be color filters.

Figure 8C:
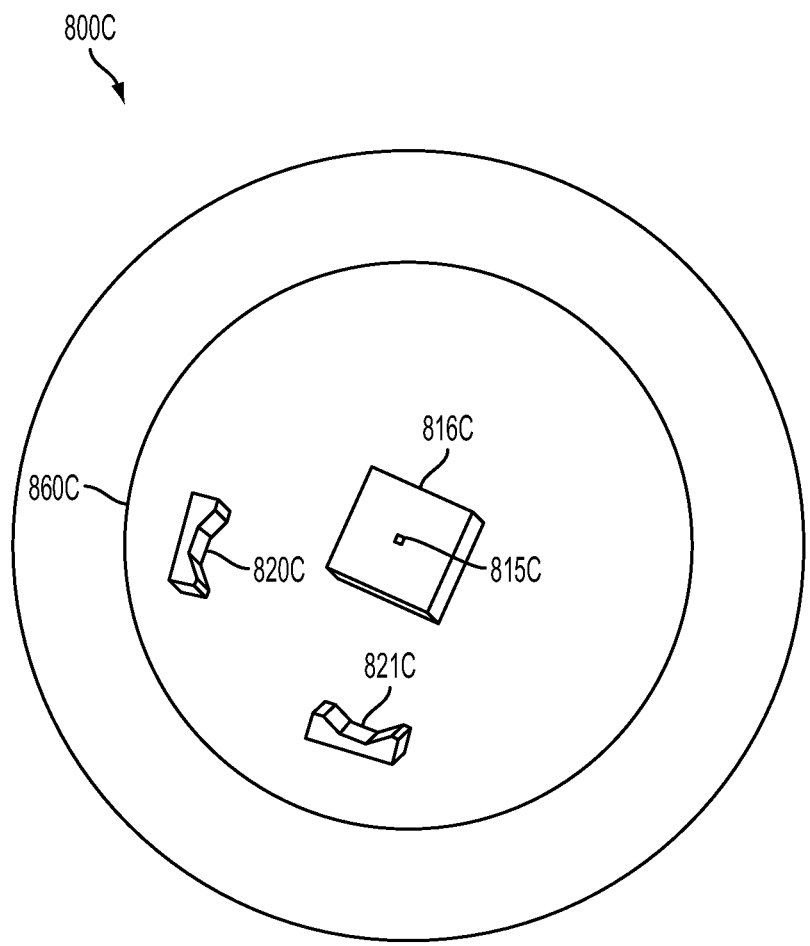

FIG. 8C shows another example embodiment of a disclosed apparatus. Base plate 860C is connected to transparent optical region 816C (cross-section shown in FIG. 8C that also shows transparent fluidic channel 815C) and optical components 820C and 821C. In the embodiment illustrated in FIG. 8C, optical components 820C and 821C are shown as a concave reflecting mirrors (light-redirecting elements), but, as mentioned above, any other optical component that modifies the measurement light and delivers the modified light through transparent optical region into fluidic channel 815C. Apparatus 800C in FIG. 8C can be used, for example, in a host structure that includes two sources of measurement light that can be, for example, at two different wavelengths, two different phases, two different modulations, etc.

Figure 8D:
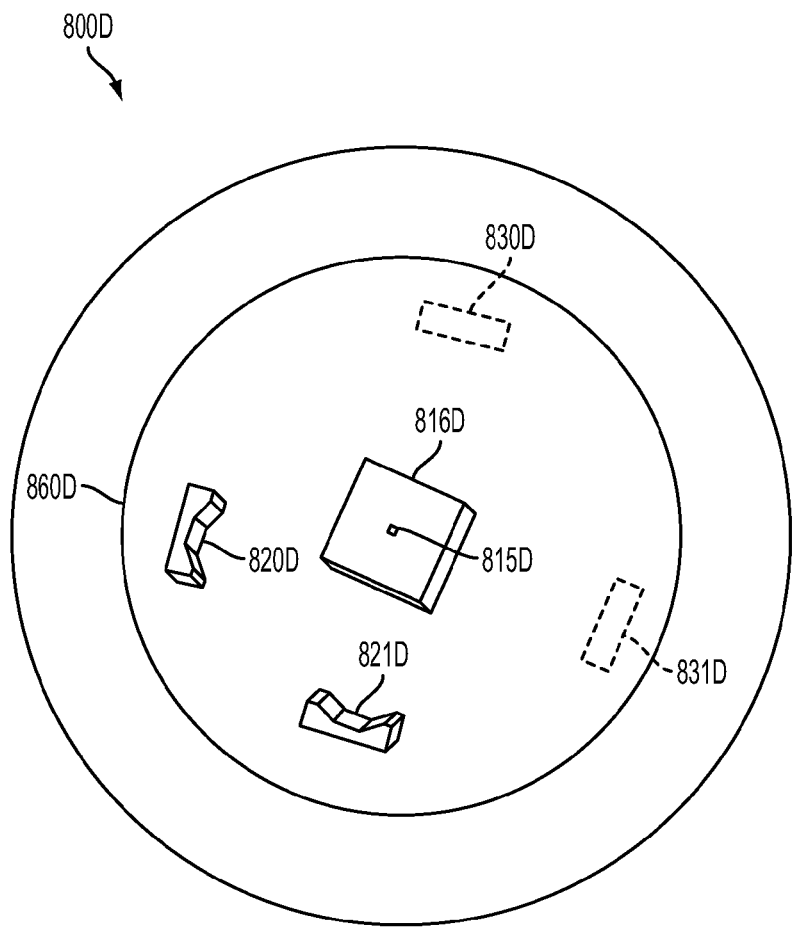

FIG. 8D shows another example embodiment of a disclosed apparatus that may also be present in a disclosed apparatus. Base plate 860D is connected to transparent optical region 816D (cross-section shown in FIG. 8D that also shows transparent fluidic channel 815D and optical components 820D and 821D). In the embodiment illustrated in FIG. 8D, optical components 820D and 821D are shown as a concave reflecting mirrors (light-redirecting elements), but, as mentioned above, any other optical component that modifies the measurement light and delivers the modified light through transparent optical region into fluidic channel 815D Apparatus 800D in FIG. 8D also includes filter assemblies 830D and 831D. These filter assemblies may take output light emanating from the objects travelling in the channel and modify it before it reaches detectors in the host structure. Filter assemblies 830D and 831D can be located on base plate 860D and can include any of the features listed above in FIG. 800B.

Figure 9A:
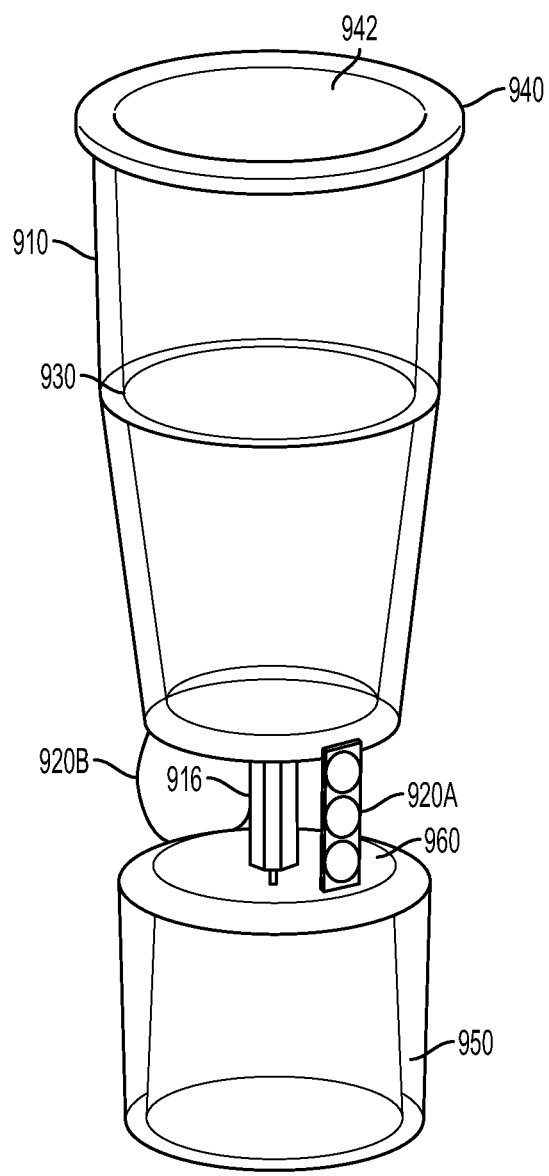
FIG. 9A is a side cross-sectional view of an example embodiment of a disclosed apparatus.
Figure 9B:
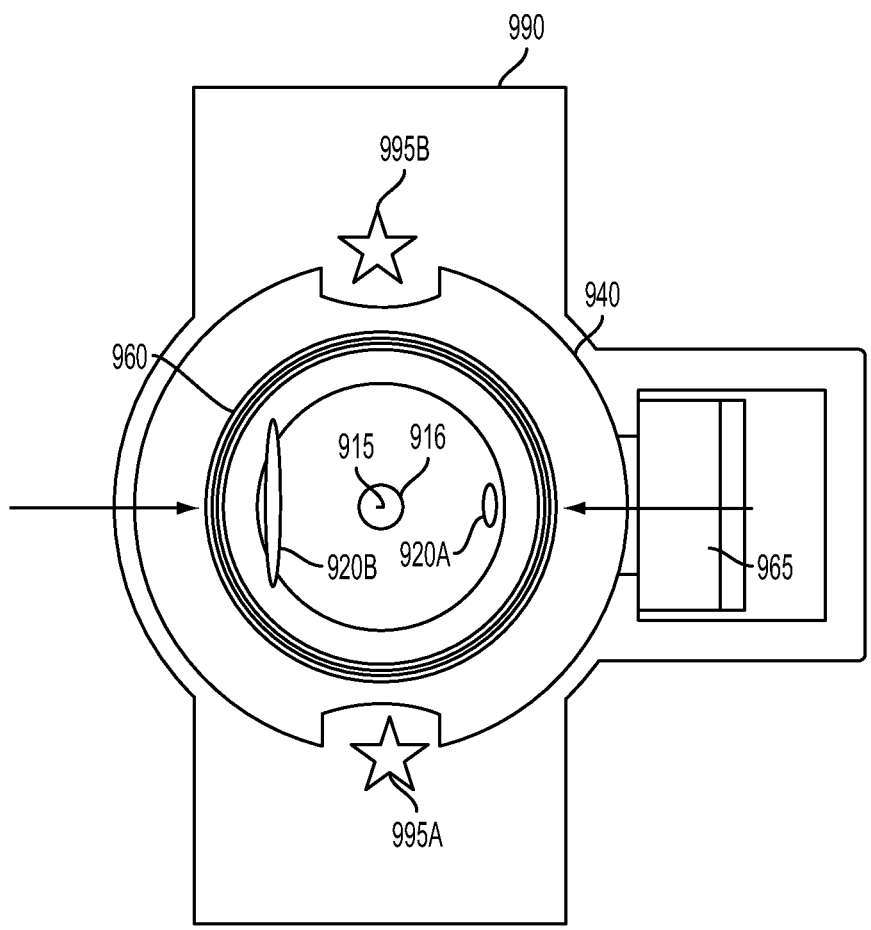
FIG. 9B is a top cross-sectional view of the same example embodiment shown in FIG. 9A.

FIGS. 9A and 9B are views of an example embodiment of a disclosed apparatus. FIG. 9A is a side perspective view of an example embodiment of a disclosed apparatus. FIG. 9B is a top cross-sectional view of the same example embodiment shown in FIG. 9A. FIG. 9A shows an embodiment of disclosed apparatus (fluidic optical cartridge) 910. Apparatus 910 includes transparent optical region 916 and transparent channel 915 (not visible in FIG. 9A) through which objects in a fluid can travel along respective paths during operation of apparatus 910. Apparatus 910 also includes two optical components 920A and 920B. In embodied apparatus 910, optical component 920A is shown as a microarray of lenses and optical component 920B is shown as a single lens element. Illustrated apparatus 910 is not limited to these specific components. Optical components 920A and 920B can be any light-redirecting element as discussed above. In some embodiments, the light-redirecting element can include a lens, a lens array, a microlens array, a mirror, or a micromirror array, or a combination thereof. In the embodiment shown in FIG. 9A, the light-redirecting elements can redirect measurement light from an outside source, such as a host structure, to create focus spots within transparent channel 915. Apparatus 910 has two optical components 920A and 920B for each of two beams of measurement light indicated by the two arrows (shown in FIG. 920B).

Apparatus 910 can be reversibly engaged with a host structure. The host structure (not shown in FIG. 9A but shown as 990 in FIG. 9B) can include a light source, a waveguide to deliver light to the transparent channel in transparent region 916 as shown. In the example embodiment, the host structure includes two waveguides that emanate two beams of measurement light (shown by arrows in FIG. 9B). Apparatus 910 includes flange 940 that is configured to reversibly engage with host structure 990. In some embodiments, a projecting male tapered part of the host structure, such as an air piston, can fit snugly into taper 942 and can make a seal at button shaft stop 930.

Apparatus 910 also includes mating end 950 that is configured to engage a pipettor tip. Both transparent optical region 916 (that has transparent channel 915 therewithin) and optical components 920A and 920B are fixed to base plate 960. The optical components and the transparent optical region are in a fixed relationship with each other facilitating the use of the cartridge in the host structure since important optical alignments in the cartridge are molded into the piece. The two beams of measurement light (arrows in FIG. 9B) in host structure 990 are opposite each other and impinge upon optical components 920A and 920B respectively. Also shown in FIG. 9B are two detectors 995A and 995B that, in the illustrated embodiment are at 90 degrees to the two beams of measurement light and can measure, for example, fluorescent, scattering, or other light emanating from objects traveling in the transparent channel within transparent optical region 915.

Figure 10A:
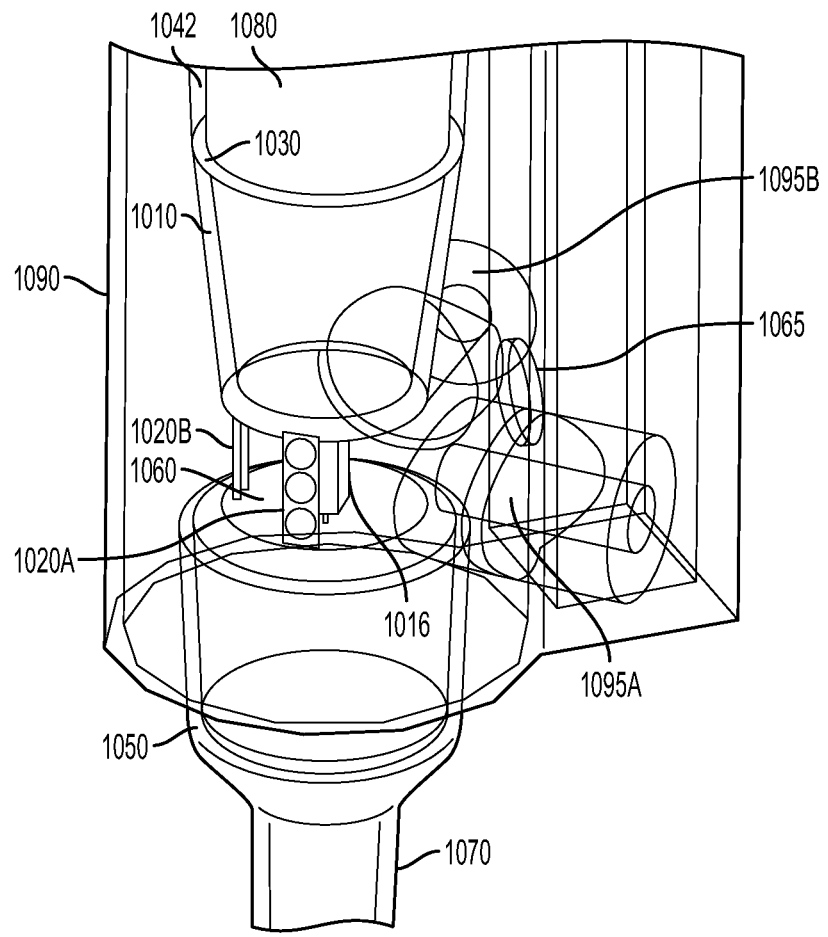
FIG. 10A is a side cross-sectional view of another example embodiment of a disclosed apparatus.
Figure 10B:
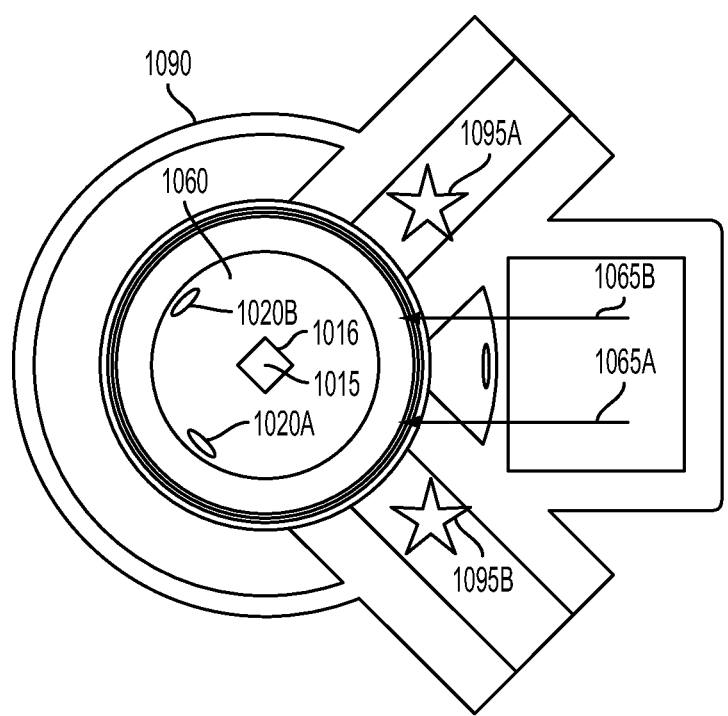
FIG. 10B is a top cross-sectional view of the same example embodiment shown in FIG. 10A.

FIGS. 10A and 10B are cutaway views of an example embodiment of a disclosed apparatus. FIG. 10A is a side cross-sectional view of an example embodiment of a disclosed apparatus. FIG. 10B is a top cross-sectional view of the same example embodiment shown in FIG. 10A. FIG. 10A shows an embodiment of disclosed apparatus (fluidic optical cartridge) 1010 inside host structure 1090 (partially cut away). Apparatus 1010 includes transparent optical region 1016 and transparent channel 1015 (not visible in FIG. 10A) through which objects in a fluid can travel along respective paths during operation of apparatus 1010. Apparatus 1010 also includes two optical components 1020A and 1020B. In the illustrated apparatus 1010, optical components 1020A and 1020B are shown as microarrays of lenses. Illustrated apparatus 1010 is not limited to these specific components. Optical components 1020A and 1020B may be any light-redirecting element as discussed above. In the embodiment shown in FIG. 10A, the light-redirecting elements can redirect measurement light from an outside source (host structure) to the objects traveling through transparent channel 1015 within transparent optical region 1016. Apparatus 1010 has two optical components 1020A and 1020B for each of two beams of measurement light indicated by the two arrows (shown in FIG. 1020B).

Apparatus 1010 can be reversibly engaged with a host structure. The host structure 1090 can include a light source, a waveguide to deliver light to the transparent channel in transparent optical region 1016 as shown. In the example embodiment, the host structure includes two waveguides that emanate two beams of measurement light (shown by arrows in FIG. 10B). Apparatus 1010 is configured to reversibly engage with host structure 1090. Apparatus 1010 also includes button shaft stop 1030. In some embodiments, a button shaft 1080 of host structure 1090 can fit snugly into taper 1042 and can make a seal with taper 1042.

Apparatus 1010 also includes mating end 1050 that is configured to engage pipettor tip 1070. Both transparent optical region 1016 (that has transparent channel 1015 therewithin) and optical components 1020A and 1020B are fixed to base plate 1060. The optical components and the transparent optical region are in a fixed relationship with each other facilitating the use of the cartridge in the host structure since important optical alignments in the cartridge are molded into the piece. The two beams of measurement light (arrows in FIG. 10B) in host structure 1090 are opposite each other and impinge upon optical components 1020A and 1020B respectively. In some embodiment, light can be reflected, either through a reflective surface that is printed, stamped, or deposited on apparatus 1010 or through a light guide (not shown) to the measurement area (transparent channel 1015). Alternatively, Also shown in FIG. 10B are two detectors 1095A and 1095B that, in the illustrated embodiment are at 45 degrees to the two beams of measurement light and can measure, for example, scattering emanations from objects traveling in the transparent channel within transparent optical region 1016.

Figure 11:
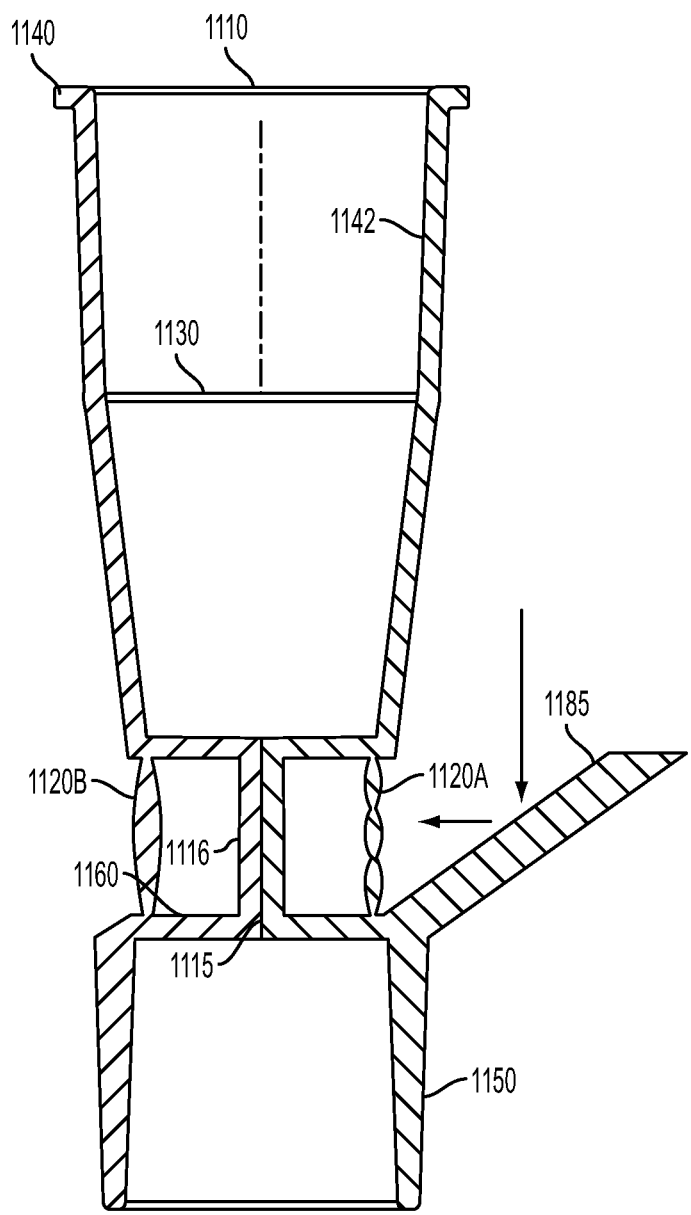
FIG. 11 is a side cutaway view of another example embodiment of a disclosed apparatus.

FIG. 11 is a side cutaway view of another example embodiment of a disclosed apparatus (fluidic optical cartridge). Apparatus 1110 includes transparent optical region 1116 having transparent channel 1115 therewithin through which objects in a fluid can travel along respective paths during operation of apparatus 1110. Apparatus 1110 also includes two optical components 1120A and 1120B. In embodied apparatus 1110, optical component 1120A is shown as a microarray of lenses and optical component 1120B is shown as a single lens element. Illustrated fluidic optical cartridge 1110 is not limited to these specific components. Optical components 1120A and 1120B can be any light-redirecting element as discussed above. In the embodiment shown in FIG. 11, the light-redirecting elements can redirect measurement light from an outside source (host structure) to the objects traveling through transparent channel 1115 within transparent optical region 1116. Apparatus 1110 also includes light-redirecting element 1185 that can redirect light (see arrows) from the host structure so that it impinges upon optical component 1120A (or 1120B) which can then focus light on objects traveling in transparent channel 1115. Light-redirecting element 1185 can be a mirror, lens, lens array, waveguide, or any other light-redirecting element and can be integrated into apparatus 1110. This can eliminate the need for the measurement light to be reflected by the host structure. In some embodiments, there can be more than one light redirecting element. In some embodiments, the light source can be in an ejector arm of the host structure.

Apparatus 1110 can be reversibly engaged with a host structure. The host structure (not shown in FIG. 11 can include a light source, a waveguide to deliver light to the light-redirecting element 1185 which then delivers light to transparent channel 1115 within which objects in a fluid travel. Apparatus 1110 includes flange 1140 that is configured to reversibly engage with the host structure. Apparatus 1110 also includes button shaft stop 1130 that can seal when apparatus 1110 is engaged with a male tapered part of the host structure. In some embodiments, a projecting male tapered part of the host structure, such as part of an air piston cylinder, can fit snugly into taper 1142.

Apparatus 1110 also includes mating end 1150 that is configured to engage an pipettor tip. Both transparent optical region 1116 (that has transparent channel 1115 therewithin) and optical components 1120A and 1120B are fixed to base plate 1160. The optical components and the transparent optical region are in a fixed relationship with each other facilitating the use of the cartridge in the host structure since important optical alignments in the cartridge are molded into the piece.

Figure 12:
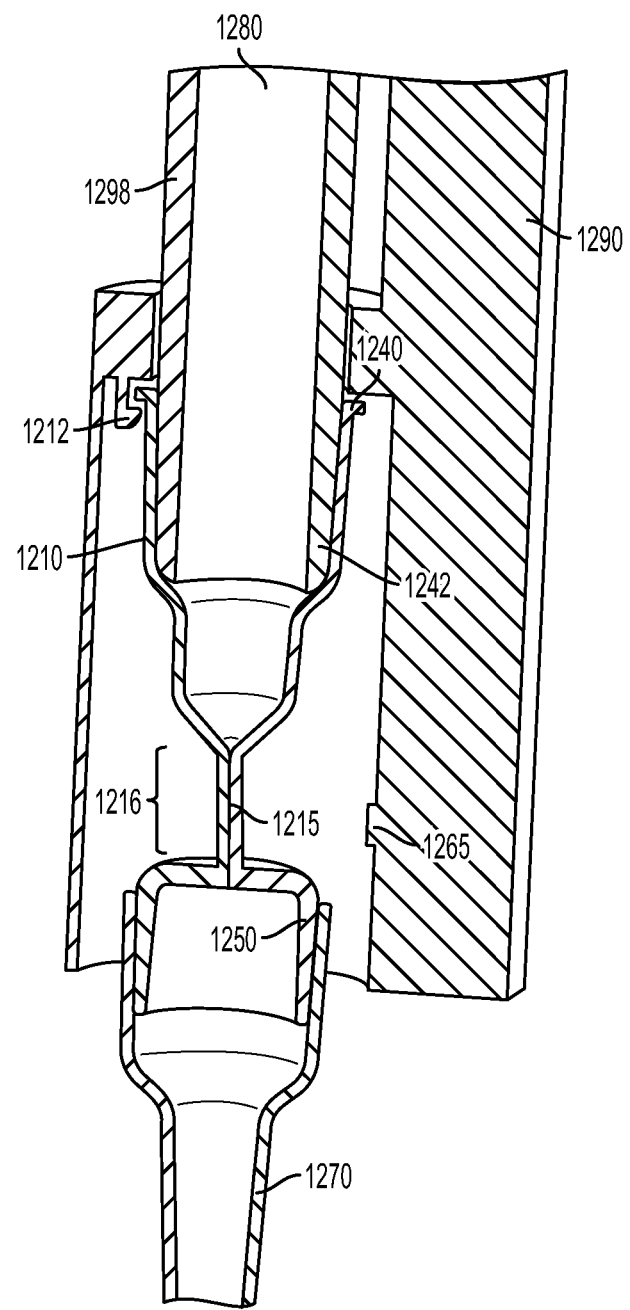
FIG. 12 is a cross-sectional cut-away view of an example embodiment of an apparatus engaged in a host structure.

FIG. 12 is a cross-sectional cut-away view of an example embodiment of an apparatus engaged in a host structure. In some embodiments, the apparatus can be a fluidic optical cartridge. Fluidic optical cartridge 1210 includes transparent optical region 1216 that has transparent channel 1215 therewithin. Fluidic optical cartridge 1210 also includes taper 1242 that has flange 1240 that is engaged with interlock tab 1212 of host structure 1290. Host structure 1290 is only partially shown in FIG. 12. Fluidic optical cartridge 1210 also has mating end 1250 that, in this embodied illustration, is mated to pipettor tip 1270. Optical components, that are also part of fluidic optical cartridge 1210 and are shown in FIGS. 6, 7, and 8A-8D are not shown in FIG. 12.

Host structure 1290 is part of an ejector arm that both can lock with fluidic optical cartridge 1210 and hold itself into position with interlock tab 1212 and can, in an additional step, eject fluidic optical cartridge 1210 from host structure 1290. Host structure 1290 also includes air cylinder 1280 inside of which an air piston (not shown in FIG. 12) snugly fits. Air cylinder 1280 can have male taper 1298 of host structure 1290 that can engage with a mating female taper on optical fluidic cartridge 1210 as shown in FIG. 12. Pipettor tip 1270 also makes an air-tight seal with mating end 1250 of fluidic optical cartridge 1210 as shown. Host structure 1290 also includes a waveguide that provides measurement light to waveguide portal 1260. Light emanating from waveguide portal 1260 impinges upon objects traveling through transparent channel 1215 in transparent optical region 1216 of fluidic optical cartridge 1210. The light may also interact with other optical components fixedly attached to fluidic optical cartridge 1210 as shown in FIGS. 6, 7, and 8A-D.

Figure 13:
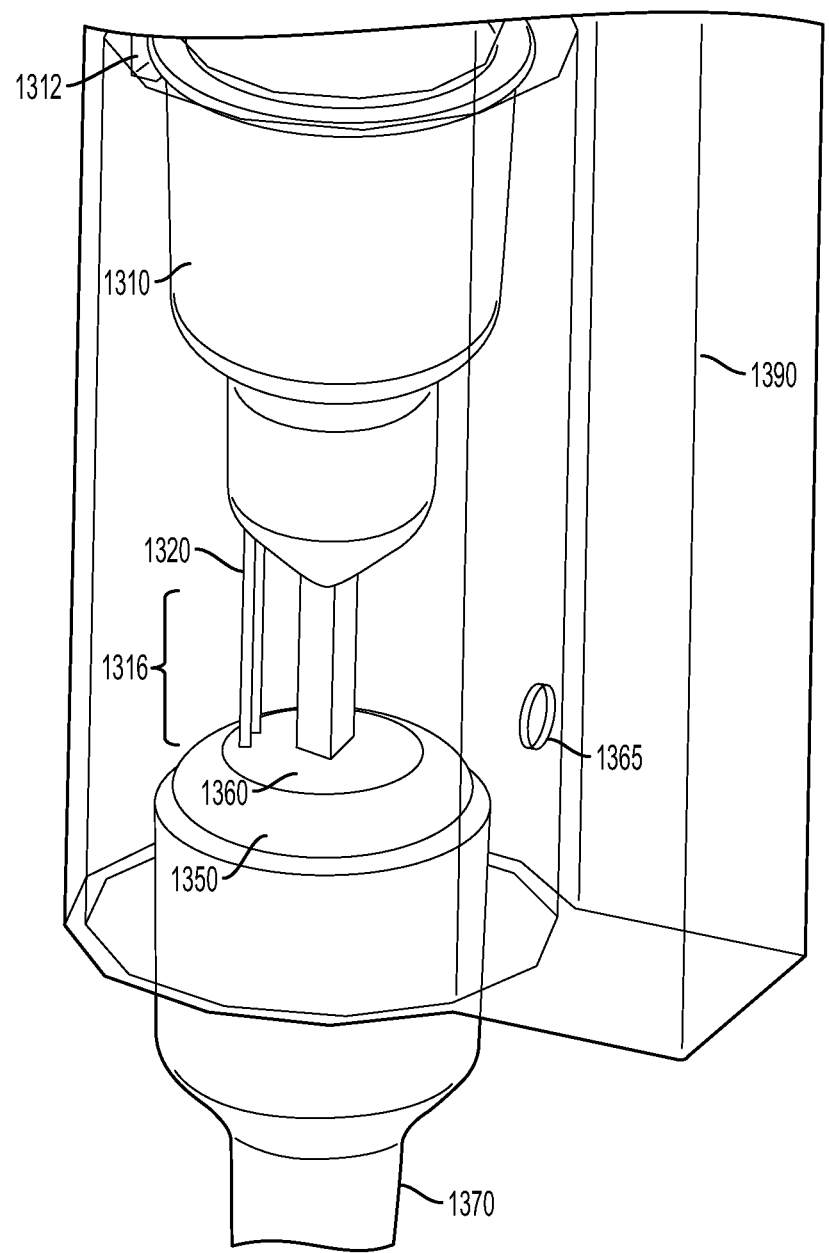
FIG. 13 is a see-through perspective drawing of an example embodiment of an apparatus engaged in a host structure.

FIG. 13 is a see-through perspective drawing of an example embodiment of an apparatus engaged in a host structure. In some embodiments, the apparatus can be a fluidic optical cartridge. Fluidic optical cartridge 1310 includes transparent optical region 1316 that has transparent channel 1315 therewithin. Fluidic optical cartridge 1310 also includes a taper that has flange 1340 that is engaged with interlock tab 1312 of host structure 1390. Host structure 1390 is only partially shown in FIG. 13. Fluidic optical cartridge 1310 also has mating end 1350 that, in this embodied illustration, is mated to pipettor tip 1370. Optical component 1320 that is also part of fluidic optical cartridge 1310 is also visible in FIG. 13.

Host structure 1390 can lock with fluidic optical cartridge 1310 and hold itself into position and can, in an additional step, eject fluidic optical cartridge 1310 from host structure 1390. FIG. 13 is an illustration of host structure 1390 that is in the "measure" mode. Host structure 1390 also includes a waveguide that provides measurement light to waveguide portal 1360. Measurement light emanating from waveguide portal 1360 impinges is redirected by optical component 1320 so that it impinges upon objects traveling through transparent channel 1315 in transparent optical region 1316 of fluidic optical cartridge 1310. Output light emanates from transparent optical region 1316 and is detected by a detector (not shown) in host structure 1390.

Figure 14:
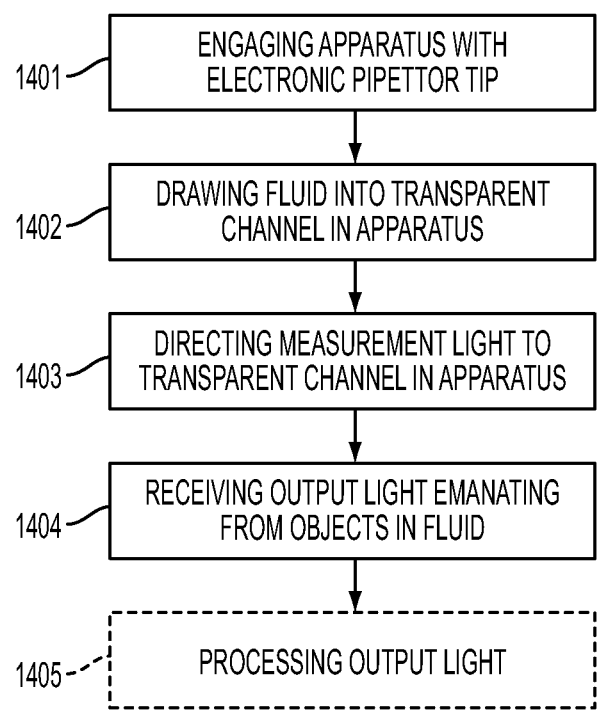
FIG. 14 is a flow diagram of an example embodiment of a disclosed method.

In another aspect, a method of using the apparatus is disclosed. FIG. 14 is a flow chart of the disclosed method that includes engaging an apparatus with a pipettor tip 1401. The apparatus is described above and includes a fluidic structure that has a transparent channel through which objects can travel along respective paths during operation of the apparatus. The apparatus also includes at least one optical component configured to provide measurement light to objects traveling through the transparent channel. The apparatus is configured to reversibly engage with a host structure. Embodiments of suitable host structures are disclosed, for example, in U.S. Pat. No. 9,261,452, filed on the same day herewith. The host structure has a source of the measurement light and electronics to process output light emanating from the objects traveling through the transparent channel. The method further includes drawing fluid into the transparent channel of the apparatus 1402. The fluid can be any analyte fluid of interest and can include, for example, biological analyte fluids from human, animal, plant, environmental and industrial sources. These fluids can include blood, plasma, serum, saliva, sperm, mucosal fluid, urine, excrement, exudate (e.g. pus), sap, nectar, juice, interstitial fluid, spinal fluid, beverages, cell culture medium, surface water, drinking water, ocean water, process water, bioreactor content, liquid pharmaceutical formulations and their precursors. Measurement light can then be directed to the transparent channel in the apparatus 1403. The light then can interact with objects traveling in the transparent channel so that output light emanates from the objects and is received by a detector in the host structure 1404. The output light can emanate from interactions with the particles and can be measured at various angles from the measurement light. For example, the output light can include fluorescence from the objects which is typically measured at 90 degrees to the measurement light. The output light can be from measurement light scattered by the objects which can be measured at various angles from the input measurement light. Many other types of output light can be used to obtain information about the objects traveling in the transparent channel.

Optionally, the disclosed method can also include processing the output light 1405. The processing typically is done using electronics in the host structure but, in some embodiments, can include elements that may be a part of the disclosed apparatus. In some embodiment, the processing can use spatial modulation.

Although specific embodiments have been illustrated and described herein, it will be appreciated by those of ordinary skill in the art that a variety of alternate and/or equivalent implementations can be substituted for the specific embodiments shown and described without departing from the scope of the present disclosure. This application is intended to cover any adaptations or variations of the specific embodiments discussed herein. Therefore, it is intended that this disclosure be limited only by the claims and the equivalents thereof.

What is claimed is:

1. An apparatus configured to engage with a host structure, the apparatus comprising:
   a base plate;
   a fluidic structure that includes:
      a channel having a cross-section dimension through which objects can travel along respective paths during operation of the apparatus, the channel having at least one transparent wall;
      a first end portion affixed to the base plate, and comprising an inlet coupled to a first end of the channel, wherein the inlet is configured to engage a pipettor tip;
      a second end portion coupled to a second end of the channel, the second end of the channel positioned opposite the first end of the channel, the second end portion having a cross-section dimension larger than the cross-section dimension of the channel; and
      a flange coupled to the second end portion and configured to reversibly engage with the host structure;
   at least one optical component affixed to the base plate and disposed in a fixed spatial relationship with the fluidic structure, and disposed in a path of measurement light, the measurement light passing from the optical component into the fluidic structure through the transparent wall to the objects traveling through the channel, output light emanating from the objects traveling in the channel in response to the measurement light and passing out of the fluidic structure through the transparent wall; and
   at least one optical filter assembly positioned directly in contact with the at least one transparent wall.

2. An apparatus according to claim 1, wherein the optical component comprises a lens that redirects the measurement light toward the transparent wall.

3. An apparatus according to claim 1, further comprising at least one optical filter assembly disposed in a path of one or more of the measurement light and the output light and affixed to the base plate, the at least one optical filter assembly configured to optically filter one or more of the measurement light and the output light.

4. An apparatus according to claim 3, wherein the at least one filter assembly is disposed opposing the transparent wall of the channel.

5. An apparatus according to claim 1, wherein the channel comprises the at least one optical filter assembly.

6. An apparatus according to claim 1, wherein the measurement light comes from a laser, a laser diode, a light-emitting diode, a superluminescent diode, a diode-pumped solid state laser, a frequency-doubled laser, a frequency-tripled laser, or a frequency-quadrupled laser.

7. An apparatus according to claim 1, wherein the at least one optical component comprises two optical components, each of the optical components being configured to receive measurement light from a different light source than the other optical component.

8. An apparatus according to claim 1, comprising two or more optical components.

9. An apparatus according to claim 1, wherein the at least one filter assembly comprises a spatial filter.

10. An apparatus according to claim 3, wherein the fluidic structure and the at least one optical filter assembly are in a fixed spatial relationship to each other.

11. An apparatus according to claim 1, wherein the second end portion comprises a taper.

12. An apparatus according to claim 1, wherein the flange is configured to engage and interlock with an interlock tab of the host structure.

13. An apparatus according to claim 1, wherein the apparatus comprises polycarbonate, poly(methyl methacrylate), polypropylene, or polyethylene.

14. An apparatus according to claim 1, wherein the optical component comprises a lens array that redirects the measurement light toward the transparent wall.

15. An apparatus according to claim 1, wherein the optical component comprises a microlens array that redirects the measurement light toward the transparent wall.

16. An apparatus according to claim 1, wherein the optical component comprises a mirror that redirects the measurement light toward the transparent wall.

17. An apparatus according to claim 1, wherein the optical component comprises a micromirror array that redirects the measurement light toward the transparent wall.

* * * * *